US005558627A

United States Patent [19]
Singer et al.

[11] Patent Number: 5,558,627
[45] Date of Patent: Sep. 24, 1996

[54] ORTHOPAEDIC BRACE WITH AN INFLATABLE AIR BAG

[76] Inventors: Samuel Singer, 125 Timber Springs La.; Jeffrey A. Fried, 499 S. Ben Franklin Rd., both of Indiana, Pa. 15701

[21] Appl. No.: 162,562

[22] Filed: Dec. 6, 1993

Related U.S. Application Data

[63] Continuation-in-part of Ser. No. 861,722, Apr. 1, 1992, Pat. No. 5,267,946, which is a continuation-in-part of Ser. No. 662,879, Mar. 1, 1991, Pat. No. 5,133,341.

[51] Int. Cl.[6] .................................................. A61F 5/00
[52] U.S. Cl. ........................... 602/13; 602/16; 602/26; 602/5; 128/DIG. 20; 607/48; 2/DIG. 3
[58] Field of Search .................................. 602/5, 13, 16, 602/23, 26; 601/151, 152; 2/2, DIG. 3; 607/48, 49; 128/DIG. 20

[56] References Cited

U.S. PATENT DOCUMENTS

| | | | |
|---|---|---|---|
| 4,393,867 | 7/1983 | Baron | 602/13 |
| 4,637,074 | 1/1987 | Taaheri. | |
| 4,685,151 | 8/1987 | Kincheloe. | |
| 4,697,808 | 10/1987 | Larson et al. | 607/49 X |
| 4,760,850 | 8/1988 | Phillips et al. | 607/49 |
| 4,872,448 | 10/1989 | Johnson, Jr.. | |
| 4,938,207 | 7/1990 | Vargo | 602/26 |
| 4,984,821 | 1/1991 | Kim et al.. | |
| 5,091,992 | 3/1992 | Pusic. | |
| 5,125,400 | 6/1992 | Johnson, Jr.. | |
| 5,133,084 | 7/1992 | Martin. | |
| 5,230,695 | 7/1993 | Silver et al. | 602/26 X |

OTHER PUBLICATIONS

Popular Science, May 1993, p. 16.

Primary Examiner—Linda C. Dvorak
Attorney, Agent, or Firm—Richard V. Westerhoff; Eckert Seamans Cherin & Mellott

[57] ABSTRACT

An orthopaedic brace for a joint includes a support mechanism attached to limb members on either side of the joint for providing support to the joint and for permitting a predetermined range of movement of the joint. The support mechanism defines a void space substantially surrounding the joint between the support mechanism and the joint. An inflatable air bag that preferably includes several air cells substantially surrounds the joint in the void space. At least one sensor attached to the support mechanism provides a trigger signal in response to a predetermined, potentially injurious condition, such as a severe force, stress, strain or acceleration. An inflation mechanism operatively connected to the air bag and the sensor inflates the air bag in response to the trigger signal, thereby providing additional support to the joint before the joint is injured.

22 Claims, 6 Drawing Sheets

FIG.1

FIG_2

FIG. 3

FIG_4

FIG_5

FIG_6

FIG_7

ORTHOPAEDIC BRACE WITH AN INFLATABLE AIR BAG

CROSS REFERENCE TO RELATED APPLICATION

This Application is a continuation-in-part of U.S. application Ser. No. 07/861,722, filed Apr. 1, 1992, now U.S. Pat. No. 5,267,946, entitled "KNEE BRACE WITH ADJUSTABLE RIGID POSTERIOR STRUT", which is a continuation-in-part of U.S. application Ser. No. 07/662,879, filed Mar. 1, 1991, entitled "KNEE BRACE WITH POSTERIOR STRUT", which issued as U.S. Pat. No. 5,133,341 on Jul. 28, 1992.

BACKGROUND OF THE INVENTION

1. Field of the Invention

This invention relates to orthopaedic braces, and, in particular, to orthopaedic braces that include an inflatable air bag wrapped around a joint or appendage supported by the brace and responsive to an abnormal condition capable of injuring the joint or appendage.

2. Description of the Prior Art

Orthopaedic braces are typically used to provide additional support to a joint that, due to prior injury, defect, surgery or other cause, does not provide normal support or that limits the normal range of motion of a limb connected to the joint. For example, the knee brace invented by us and disclosed in U.S. Pat. No. 5,133,341, herein included by reference, provides support for the knee without undue restriction on the natural kinematics of the knee. The brace includes a rigid posterior strut located in the popliteal space of the knee to which vertical supports are connected by hinges. Application Ser. No. 07/861,722, filed Apr. 1, 1992, to issue as U.S. Pat. No. 5,267,946 and herein included by reference, discloses a similar type of knee brace that can be adjusted to fit knee joints of different sizes and shapes. These braces are very useful for prophylactic, functional and rehabilitative purposes. However, these braces and other types of passive restraint braces do not include any mechanism that would protect against an abnormal, severe, lateral or torsional force, stress, strain or acceleration that can potentially cause further injury to the joint, or protect against tearing of the muscle connected to the joint, except for the normal travel limits of extension and flexion.

Inflated air bags, or air cells, can provide a high degree of support to protect against such potentially injury causing conditions. Some types of braces include inflatable air bags surrounding selected portions of the joint to provide support to the joint. U.S. Pat. No. 4,872,448, to Johnson, Jr., discloses a knee brace with a U-shaped inflatable air cell engaging the knee above and along opposed sides of the patella. The air cell is inflated to a desired pressure and remains in that condition during use. U.S. Pat. No. 5,125,400, also to Johnson, Jr., discloses an ankle brace having multiple inflatable cells that are inflated during use of the brace. However, because the air cells of these devices remain inflated during use, the range of motion of the joint supported by the brace is reduced (for high inflation of the air cells) or the brace provides limited support in response to an excessively stressful condition (for low inflation of the air cells).

There are also a variety of safety devices that include air cells that inflate in response to a potentially injury-causing condition. U.S. Pat. No. 5,133,084, to Martin, discloses an inflatable safety collar device for use primarily by motorcyclists. Inflation is triggered by a pull string which may be attached to a vehicle for operation during a crash or collision. U.S. Pat. No. 4,984,821, to Kim et al., discloses a suit to be worn by motorcyclists that has air cells contained between the layers of cloth in the pants and jacket. Similar to Martin, the air cells are inflated when a pull string attached to the vehicle is tensioned. These devices fail to provide support for a joint during normal use. Needless to say, the above-described collar and suit become awkward to wear if the rider forgets to disengage the pull cord before dismounting the vehicle.

Therefore, there is a need for an orthopaedic brace that provides support to a joint and full, normal range of movement during normal use, and that also provides additional support to the joint in response to an excessive force, stress, strain or acceleration that may otherwise injure the joint.

There is an additional need for a brace that can quickly stimulate muscles connected to the joint in response to an excessive lateral or torsional force, stress, strain or acceleration to preload the muscle in preparation for the excessive condition and thereby avoid possible damage to the muscle.

SUMMARY OF THE INVENTION

These needs and others are satisfied by the invention which is directed to an orthopaedic brace for a joint that includes a support mechanism, attached to limb members on either side of the joint, for providing support to the joint and for permitting a predetermined range of movement of the joint. The support mechanism defines a void space substantially surrounding the joint between the support mechanism and the joint. An inflatable air bag that preferably includes a plurality of separate cells is emplaced in the void space. A sensor system attached to the support mechanism provides a trigger signal in response to a predetermined condition or set of conditions, such as a severe lateral or torsional force, stress, strain, or acceleration that is capable of injuring the joint. An inflation mechanism operatively connected to the air bag and the sensor system inflates the air bag in response to the trigger signal.

According to another aspect of the invention, an orthopaedic brace attached to limb members on either side of a joint includes a support mechanism for providing support to the joint and for permitting a predetermined range of movement of the joint. A muscle stimulator system has one or more muscle stimulators located against the skin adjacent to one or more muscles connected to the joint. A sensor system attached to the support mechanism provides a stimulator trigger signal in response to a predetermined condition or set of conditions, such as a severe force, stress, strain or acceleration, that is capable of injuring the muscle. The stimulator trigger signal activates the muscle stimulator system to stimulate the muscle or muscles before severe damage to the muscle or muscles can occur.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Air bag and inertial sensor technology has been developed to a high level of reliability. Miniaturized sensors are available that can be incorporated into almost any device, with or without intelligent microprocessor control. Typical large volume passenger air bags used in automobiles can be inflated in about 50–55 msec. Because damage to joints typically occurs in a time frame much greater than the time necessary to inflate a small air bag, a time period significantly smaller than the time to inflate an automobile passenger air bag, this technology is particularly appropriate for incorporation into orthopaedic braces. For example, anterior cruciate ligament damage typically occurs after about 70 msec of excessive stress, and a small air bag suitable for a knee brace would only take about 10–15 msec to inflate.

Typical prior art brace systems using rigid brace members cannot incorporate an air bag because those braces are typically designed to operate only if molded to or tightly fitted to the leg, leaving no room for sensors or expansion of an air bag between the leg and the frame of the brace. For example, insertion of an air bag in a non-posterior strut type of knee brace would interfere with the normal fit and function of such a brace.

The preferred embodiment described herein is an improvement upon the knee braces described in our U.S. Pat. No. 5,133,341 and in our application Ser. No. 07/861,722 filed on Apr. 1, 1992, to issue as U.S. Pat. No. 5,267,946, each incorporated by reference herein. These braces have a rigid posterior strut and rigid support members that leave a void space around the knee into which an inflatable air bag can be fitted. The knee brace of the present invention incorporating an inflatable air bag around the joint provides additional support and bracing against excessive, unusual, forces, stresses, strains or accelerations that would otherwise tend to cause pathological injury to the joint or to the muscles surrounding the joint and furthermore provides some padding when not inflated.

Figure 1:
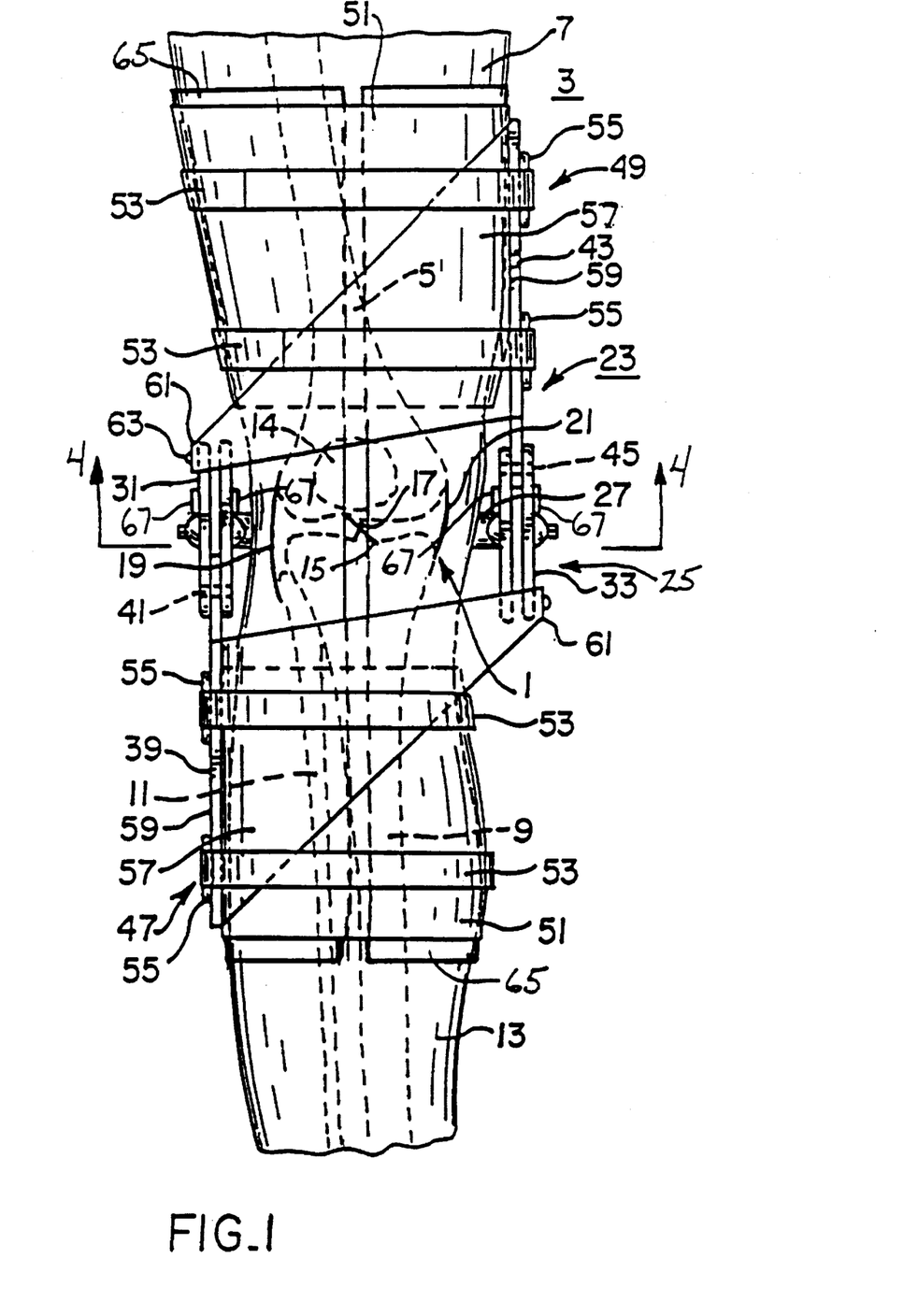
FIG. 1 is a front elevation view of a knee brace in accordance with one embodiment of the invention shown in use.
Figure 2:
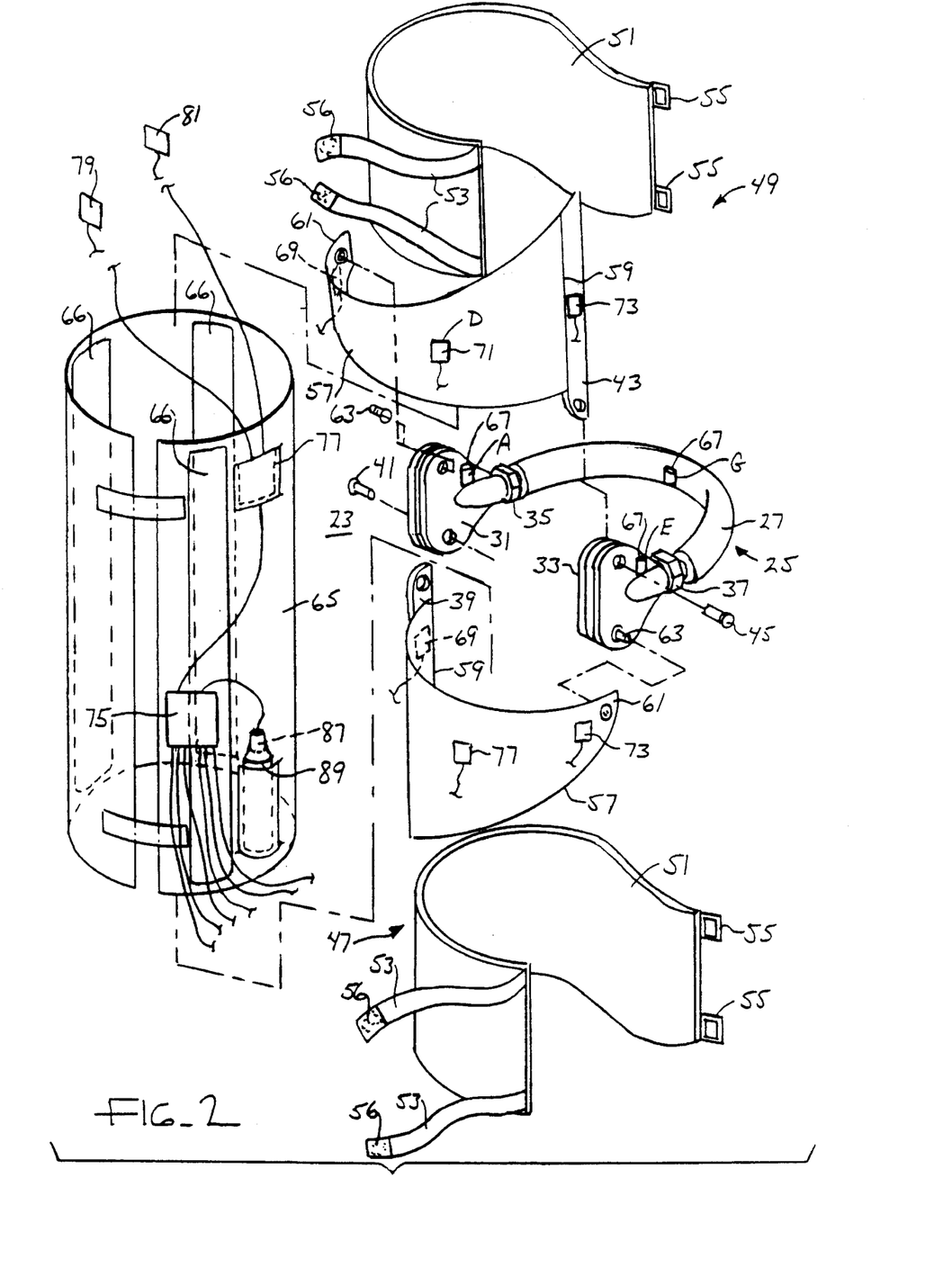
FIG. 2 is an exploded isometric view of the knee brace of FIG. 1.
Figure 3:
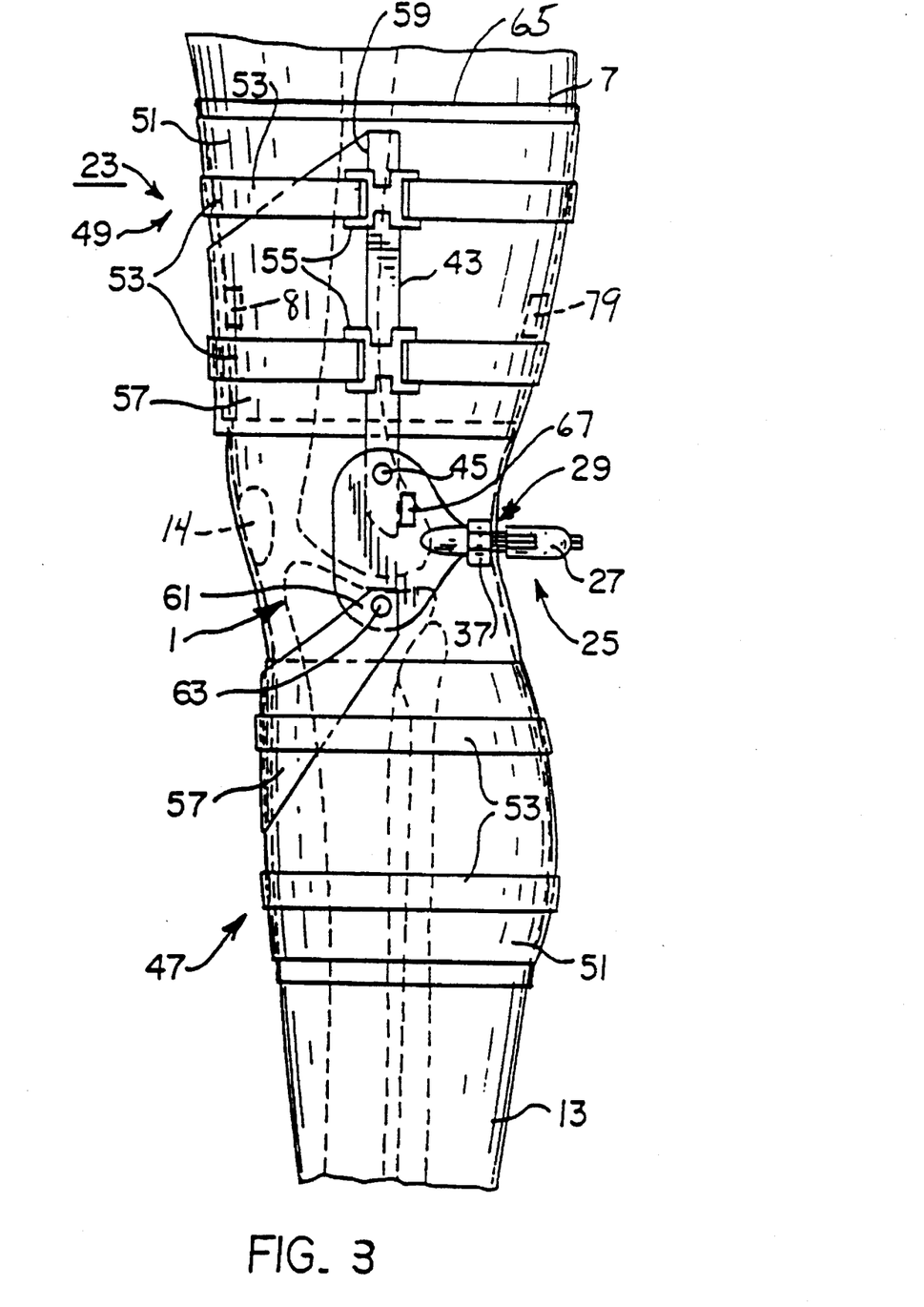
FIG. 3 is a side elevation view of a knee brace in accordance with the invention with the leg in extension.
Figure 4:
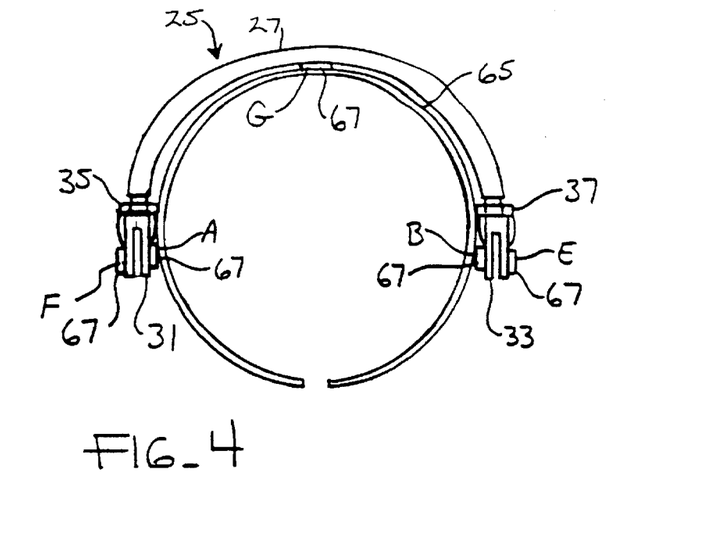
FIG. 4 is a horizontal section through line 4—4 of FIG. 1.
Figure 5:
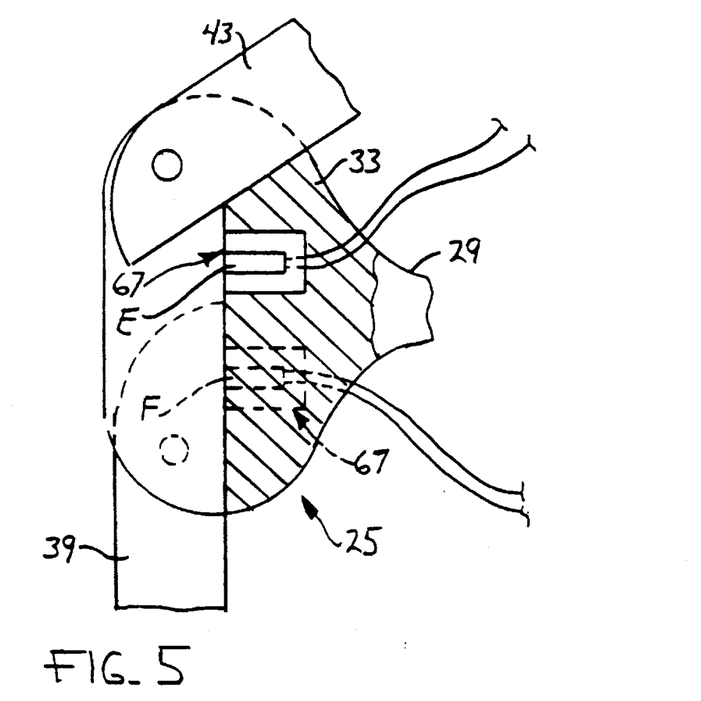
FIG. 5 is a vertical section through a terminal portion of the rear strut showing placement of pressure sensors in the hinge.

FIG. 1 illustrates a preferred embodiment of a brace in accordance with the invention in use in supporting and stabilizing a knee joint 1 of a human right lower extremity 3. The knee joint 1 is formed by the enlarged lower end of the femur 5, which is the bone of the thigh 7, and the upper end of the tibia 9 which together with the fibula 11 form the bones of the leg 13. The patella (knee cap) 14 articulates with the distal end of the femur 5. Articulation of the extremity is obtained by contraction of the large muscles (not shown) of the thigh 7, such as the quadriceps on the anterior side for extension and the hamstrings on the posterior side for contraction.

The joint 1 is held together by an arrangement of ligaments including the anterior cruciate ligament 15, the posterior cruciate ligament 17, the lateral collateral ligament 19 and the medial collateral ligament 21. Shear forces and torsional forces applied to the knee joint can result in stretching and even tearing of one or more of these ligaments. A common injury occurs when a lateral blow is applied to the outside of the thigh with the foot planted. This causes the knee joint to buckle inward, resulting in tearing of the medial collateral ligament 21, and occasionally the anterior cruciate ligament 15 as well.

The knee brace 23 shown in FIGS. 1–5 includes an adjustable rigid posterior strut 25. The strut 25 has an arcuate member 27 that extends behind the knee joint 1 through the popliteal area 29. Terminal members 31 and 33 are secured to the arcuate member 27 by mounting members 35 and 37 respectively, which are preferably adjustable. The terminal members 31, 33 are adjacent, but spaced from the lateral and medial sides, respectively of the knee joint 1.

An inferior lateral rigid elongated support member 39 is pivotally connected to the lateral terminal member 31 of the strut 25 at a first pivot point by a pivot pin 41 and extends down along the lateral side of the leg 13. A superior medial rigid elongated support member 43 is pivotally connected to the terminal member 33 of the adjustable strut 25 at a second pivot point by pivot pin 45, and extends upward medially along the thigh 7.

The support members 39, 43 are secured to the leg 13 and thigh 7 respectively by anchoring devices 47 and 49. The anchoring devices 47, 49 each include a sleeve 51 of a non-slip cushioning material, such as neoprene, and a pair of straps 53 which are threaded through buckles 55 on the support members 39, 43 and secured by a securing mechanism, such as Velcro® fasteners 56. The anchoring devices 47, 49 secure the support members 39, 43 to the fleshy portions of the leg 13 and the thigh 7, respectively, so that forces are transmitted through these support members into the large muscles of the extremity 3.

The brace 23 is also provided with a pair of stiff, semi-rigid, anterior cuff members 57. The cuff members are generally triangular in shape with one edge 59 secured to the associated elongated support member 39 or 43 and with the opposing vertex 61 pivotally connected, such as with a snap fastener 63, to a connection point on the terminal member 31 or 33 opposite to the terminal member to which the associated support member 39 or 43 is secured. The pivots formed by the fastener 63 are laterally aligned with the corresponding pivot points of the elongated members to which the cuffs are attached along the edge 59. The cuff members 57 are unsnapped and opened for applying the brace 23 to the extremity 3, and then are wrapped around and in front of the thigh and leg and snapped in place.

The above-described brace provides a void space between the knee joint and the strut 25 that extends all around the knee joint. The joint is not "captured" as in other types of knee braces. A flat, inflatable air bag 65, that preferably includes a plurality of communicating, longitudinally extending air cells 66, is wrapped around the knee joint within the structure of the posterior strut 25, fitting between the neoprene sleeve 51, or wrap, and the thigh 7, knee 1 and leg 13. The air bag 65, in the deflated state, is firmly contained within the brace structure 25, 31, 33, 39, 43, the cuffs 57, the straps 53 and the leg. The air cells 66 are arranged in the bag 65 to provide a desired shape in the inflated state.

The above-described knee brace 23 has a Z-shaped frame, or support structure, formed by the posterior strut 25 and the rigid support members 39 and 43. An alternative embodiment (not shown) has an H-shaped frame. In the alternative embodiment, an inferior medial elongated, rigid support member is pivotally attached to the medial terminal member 31 at a third pivot point below the second pivot point and extends down along the medial side of the leg 13. A superior lateral elongated, rigid support member is pivotally attached to the lateral terminal member 33 at a fourth pivot point above the first pivot point and extends upwards along the lateral side of the thigh 7. Two additional wide, semirigid cuff members 57 can be used in this embodiment to help transfer forces to the soft, fleshy parts of the thigh and leg.

The rigid Z-shaped or H-shape frame provides a platform to which sensors can be attached to measure forces acting on the knee joint. Because of the rigid frame of the posterior strut brace, which rigid members are not normally in contact with the knee joint, pressure sensors 67 can be attached to the posterior strut, the hinges and the rigid vertical support members, for example, at positions A, B, E, F and G. Strain 69, stress 71 and acceleration 73 sensors can be attached along the semirigid cuffs and between selected parts of the brace, for example, at positions C and D. The outputs of these sensors, used directly or processed in preprogrammed combinations by a microprocessor 75 (see FIG. 7), can be used to sense excessive forces capable of causing pathological injury to the joint, or to bone or muscle attached to the joint. In the event of such a condition being detected, the electronic circuits will trigger an air bag inflation system.

In normal persons inflation of the air bag 65 will also preload the muscle around the joint 1 causing the muscle to react against the excessive force, thereby providing an additional measure of defense against pathological injury. For users with pathological laxity of the joint, a muscle stimulator system can be connected to the sensor circuit to help overcome such laxity. Benefit can be obtained by stimulation of the hamstring muscle where an isolated anterior cruciate ligament rupture has been diagnosed, or by stimulation of the quadriceps muscle in a patient with an isolated posterior cruciate ligament injury. For example, a muscle stimulator system 77 capable of independently activating two electrode pads 79 and 81 to stimulate two different muscles, such as the Mentor® model MM2, could be used to stimulate the hamstring muscles at location H and the quadriceps muscle at location I a few inches above the knee joint 1. When the sensors trigger the air bag inflation system, the electrode pads will also be triggered. The controlled muscle contraction resulting from the activation of the electrode pads would act to preload the muscle to protect the joint from further damage. The brace may include the muscle stimulator system without the air bag system, but it is preferred that both systems be included in a brace.

Figure 6:
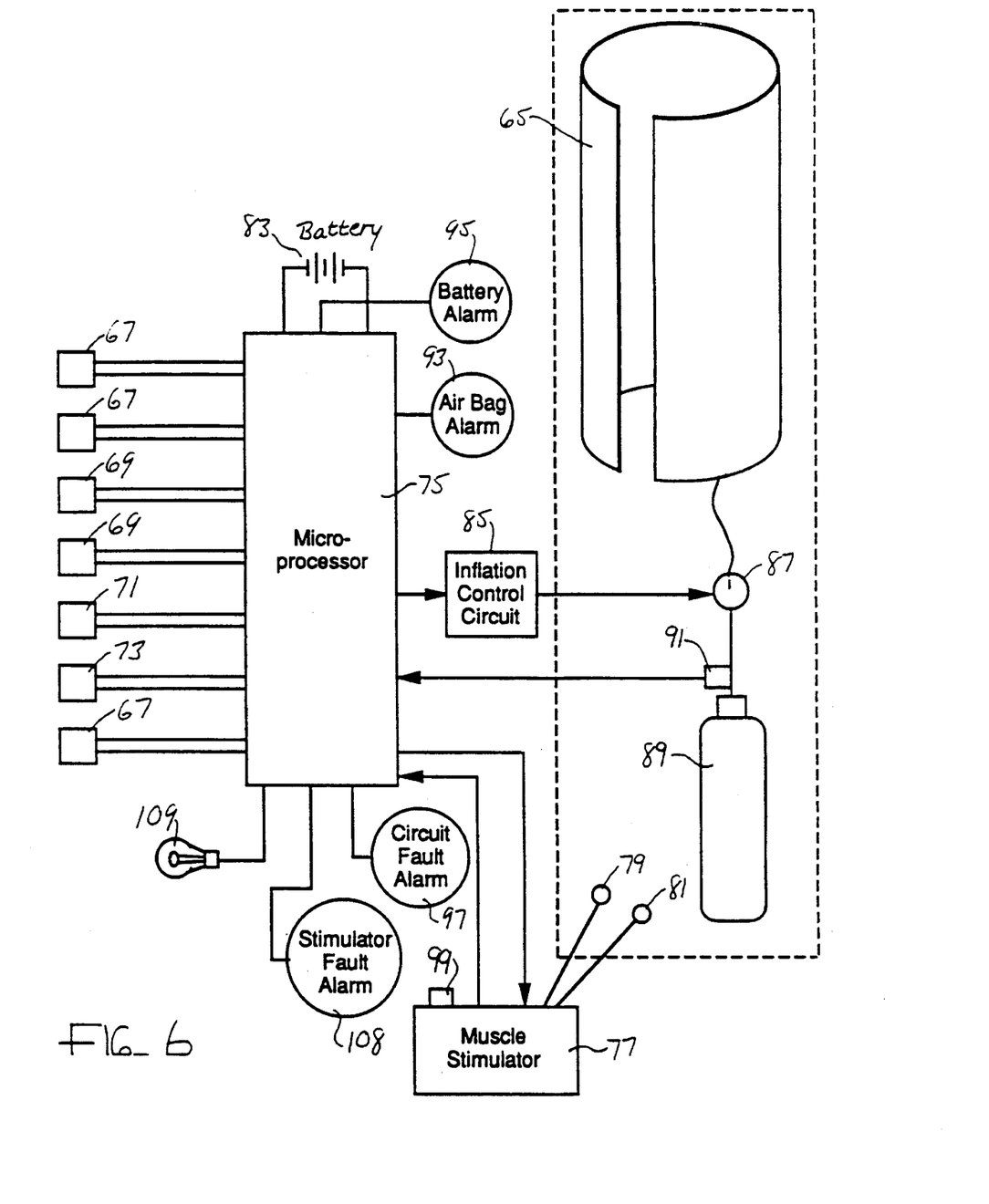
FIG. 6 is a functional schematic of the sensor circuit for triggering inflation of the air bag.

Referring now also to FIG. 6, the air bag inflation system of a preferred embodiment is a battery 83 powered circuit that includes sensors 67, 69, 71, 73 each connected to a programmable microprocessor 75. The microprocessor 75, in response to a predetermined signal from one or more of the sensors, activates an inflation control circuit 85. The inflation control circuit 85 detonates a charge of sodium azide (not shown), explosively opening a glass plug 87 in a replaceable gas cylinder 89 containing compressed nitrogen gas, thereby releasing the gas to inflate the air bag 65 within about 10–20 msec. A deflation mechanism, such as a pinhole (not shown) in the air bag 65 or a valve (not shown), permits deflation after use.

A pressure sensor 91 operatively connected to the cylinder 89 sends a signal to the microprocessor 75 for monitoring the cylinder pressure. The microprocessor 75 sends a signal to a visible or audible air bag alarm 93 if the pressure is too low for safe use of the brace 23. Similarly, a battery alarm 95 is activated if the battery 83 is low, and a fault alarm 97 is activated if any sensor is not operational or if a fault is detected in any part of the circuitry. Also operatively connected to the microprocessor is the muscle stimulator system 77 with two electrode pads 79 and 81. A manual test button 99 on the muscle stimulator system permits manual activation of the stimulators 79, 81 for testing purposes.

Special instructions can be programmed into the microprocessor 75. Sensors can be set to act individually, in specified groups or patterns, or the logic circuit can be programmed so that any specified combination of forces, or any abrupt change in the action of such forces, or rapid changes in the inertia of the joint or leg or thigh will cause the inflation of the air bag.

Figure 7:
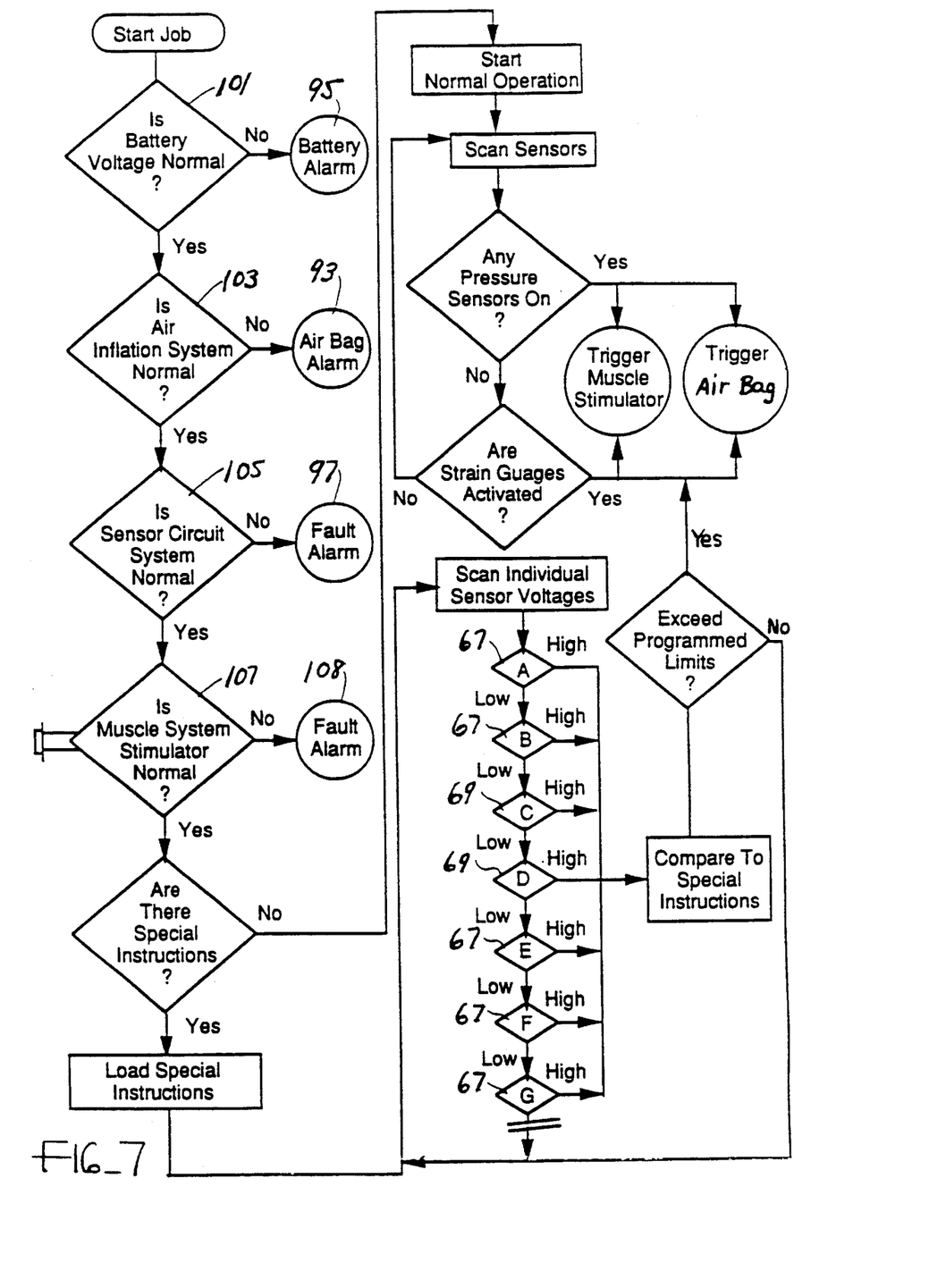
FIG. 7 is a flow chart illustrating a typical embodiment of the logic used for operation of the knee brace of this invention.

A preferred logic structure that can be programmed into the processor is illustrated in FIG. 7. When the system is turned on, a series of tests are performed to assure that all systems are operational. These checks include a battery test 101, an air bag inflation system test 103, a sensor test 105, and a muscle stimulator test 107 to briefly activate the muscle stimulator 76. A malfunction of the muscle stimulator system can be indicated by a stimulator alarm LOS. Once the tests are complete, the microprocessor 75 verifies if there are special instructions. If there are no special instructions, the system scans the sensors and activates the air bag inflation system if any pressure sensors, stress sensors, strain sensors or acceleration sensors are sending a signal indicative of a potentially injurious condition. If there are special instructions, the microprocessor activates the air bag inflation system if any combination of signals from the sensors exceed one or more sets of programmed limits. As indicated in the drawing, a normal indicator 109, such as a lamp visible to the wearer of the brace during normal operation of the brace, can be included.

The posterior strut 25 is located in the popliteal space 29. It is rigid and is designed to transfer forces around the knee joint L without interfering with the normal kinematics of the knee. When the air bag inflation process is triggered by the sensor circuits, the free space around the knee joint L will be filled in about 10–20 msec by the inflating air bag 65. This will temporarily lock the knee joint L in the existing position, supporting the joint in a cushion of pressurized gas and avoiding potential injury. The air bag 65 will subsequently deflate through the deflation mechanism, returning normal range of movement to the knee joint 1.

In operation, an excessive lateral force, such as occurs with a kick to the lateral side of the knee, will activate a pressure sensor 67 at A and cause equal outputs from strain sensors 69 at C and D. This will trigger inflation of the air bag 65 and avoid injury to the medial collateral ligament 21 and the anterior cruciate ligament 15. The muscle stimulator 77 will activate the electrode pad 81 at I, stimulating the quadriceps muscle to contract.

An excessive medial force, for example from a football tackle, will activate a pressure sensor 67 at B and cause about equal outputs from strain sensors 69 at C and D. This will trigger inflation of the air bag 65 to avoid injury to the lateral collateral ligament 19 and the anterior cruciate ligament 15. The muscle stimulator 77 will activate the electrode pad 81 at I, stimulating contracture of the quadriceps muscle.

Excessive external or internal rotational forces, occurring for example while pivoting in tennis or making abrupt turns while skating or skiing, will cause substantially different outputs from strain sensors 69 at C and D, and may also cause pressure sensors 67 at A, B, E or F to activate. This will trigger inflation of the air bag 65, locking the thigh 7, leg 13 and knee joint 1 rigidly in a fixed position to avoid ligament rupture or other pathological instability. Excessive internal or external rotation will cause the stimulator 77 to act on the hamstring muscles at H with electrode pad 79.

In the event of an excessive anterior force causing hyper-extension of the knee 1, such as may occur with a blow to the front of the knee, any or all of the pressure sensors 67 at E, F or G will activate causing inflation of the air bag 65. The hyper-extension will be restricted by the introduction of a cushion of air between the knee 1 and the posterior strut 25, thus avoiding injury to the anterior cruciate ligament 15 and the posterior cruciate ligament 17. In this case, contracture of the quadriceps will be stimulated by the stimulator 77.

For extreme conditions where a pathological instability pre-exists, special sensors can be fixed at critical locations on the Z-shaped or H-shaped frame, on the cuffs 57 or on the belts 53. Such sensors can be set to a high level of sensitivity so as to trigger inflation of the air bag 65 in the event of a specified excessive force being detected to which the user is particularly susceptible. This can serve to give confidence to a user of the brace 23 who would otherwise refrain from participation in many physical activities.

The sensitivity of the sensing and triggering circuits can be adjusted for the particular activity of the user, his or her height and weight, physical condition and ability. For example, in a high velocity sport like skiing, the overall sensitivity of sensors A and B should be reduced, and the sensitivity of sensors C and D increased. For football, one may set sensors A, B and G to high sensitivity and sensors D and E to a low level of sensitivity.

It will be appreciated that the brace of the present invention includes electronic circuitry providing functions that can be obtained in a wide variety of embodiments those skilled in the art of such devices may equivalently choose.

It will be appreciated that although the discussion of the exemplary preferred embodiments refer to knee braces and knee joints, the invention is not limited to knee braces, but rather encompasses braces for other joints and appendages also.

It will also be appreciated that although the discussion of the preferred embodiments specified sensors sensitive to specific types of conditions, such as pressure, strain, stress and acceleration, and particular locations for the placement of such sensors, the choice of sensor types, the combination of sensors used and the placement of the sensors are design choices capable of a wide variety of variation within the scope of the invention.

It will additionally be appreciated that although the air bag described above preferably contains several air cells, the invention also encompasses a brace with an air bag having a single air cell, and also a brace with a plurality of air bags that may be activated together or separately. The air bag, although it preferably extends about around the joint or appendage to be protected, may also be smaller, to protect a limited area of the joint or appendage.

It will further be appreciated that the brace of this invention may include an inflatable air bag system without including a muscle stimulator system, and also may include a muscle stimulator system without an inflatable air bag system.

Whereas particular embodiments of the present invention have been described above for purposes of illustration, it will be appreciated by those skilled in the art that numerous variations of the details may be made without departing from the invention as described in the appended claims.

We claim:

1. An orthopaedic brace for a joint joining two members, comprising:

hinged rigid support means affixed to said two members providing support to the joint and for permitting a predetermined range of movement of the joint and defining a void space substantially surrounding the joint between the support means and the joint;

an inflatable air bag in the void space;

sensor means attached to the hinged rigid support means for providing a trigger signal in response to a predetermined condition on the joint that is capable of injuring the joint; and inflation means operably connected to the sensor means and the air bag for inflating the air bag in response to the trigger signal.

2. The brace of claim 1, wherein the predetermined condition is at least one injurious condition on the joint selected from the group consisting of linear and torsional forces, strain, stress and acceleration.

3. The brace of claim 2, wherein the sensor means includes a set of discrete sensors providing a corresponding set of sensor signals, each member of the set of sensor signals being indicative of one of the injurious conditions from a corresponding member of the set of discrete sensors.

4. The brace of claim 3, wherein the sensor means further includes programmable processor means operably connected to each member of the set of discrete sensors and to the inflation means for programming a threshold sensitivity for each member of the set of discrete sensors and for providing the trigger signal in response to a programmed set of sensor signals.

5. The brace of claim 4, wherein the inflation means includes a canister containing a material for inflating the inflatable air bag, and means for providing operative connection between the inflation means and the canister in response to the trigger signal.

6. The brace of claim 5, wherein the valve means includes deflation means for deflating the inflatable air bag.

7. The brace of claim 2, further comprising muscle stimulator means having electrode means adapted to be located proximate a muscle connected to the joint for stimulating the muscle in response to a stimulator signal provided by the sensor means in response to the predetermined condition such that the muscle is preloaded for protecting the joint from the injurious condition.

8. A brace for a knee joint joining thigh and leg members, said brace comprising:

brace means adapted to be spaced apart from the knee joint for providing support to the knee joint and for permitting a predetermined range of movement of the knee joint, including:

a rigid posterior strut comprising an arcuate member adapted to extend through a popliteal space behind the knee joint and having first and second ends and a longitudinal axis, first and second terminal members and first and second mounting means fixing said first and second terminal members to said first and second ends respectively of said arcuate member;

a first rigid support member pivotally connected to said first terminal member and adapted to extend upward along a first side of the thigh member;

a second rigid support member pivotally connected to said second terminal member and adapted to extend downward along a second side of the leg member opposite the first side of the thigh member;

first support means adapted to secure said first rigid support member to the thigh member; and second support means adapted to secure said second rigid support member to the leg member;

an inflatable air bag adapted to be positioned adjacent the knee joint and substantially surrounding the knee joint;

sensor means attached to the brace means for providing a trigger signal in response to a predetermined condition that is capable of injuring the knee joint; and inflation means carried by the brace means and operably connected to the air bag and to the sensor means for inflating the air bag in response to the trigger signal from the sensor means.

9. The brace of claim 8, wherein the predetermined condition is at least one of the injurious conditions selected from the group consisting of pressure, strain, stress and acceleration.

10. The brace of claim 9, wherein the sensor means includes a set of discrete sensors for providing a corresponding set of sensor signals, each member of the set of sensor signals being indicative of one of the injurious conditions from a corresponding member of the set of discrete sensors.

11. The brace of claim 10, wherein the sensor means further includes programmable processor means operably connected to each member of the set of discrete sensors and to the inflation means for programming a threshold sensitivity for each member of the set of discrete sensors and for providing the trigger signal in response to a programmed set of sensor signals.

12. The brace of claim 11, wherein the inflation means includes a canister containing a material for inflating the inflatable air bag, and means for providing operative connection between the inflation means and the canister in response to the trigger signal.

13. The brace of claim 12, wherein the valve means includes deflation means for deflating the inflatable air bag.

14. The brace of claim 9, wherein the sensor means includes at least one of the following:

a first pressure sensor located on a medial side of the posterior strut facing the knee joint and providing a first pressure signal in response to a medial force on the knee joint;

a second pressure sensor located on a lateral side of the posterior strut facing the knee joint and providing a second pressure signal in response to a lateral force on the knee joint;

a third pressure sensor located on the posterior strut and adapted to be positioned in the popliteal space facing the knee joint and providing a third pressure signal in response to a posterior force on the knee joint;

a fourth pressure sensor located on the first terminal member proximate the first rigid support member and providing a fourth pressure signal in response to a force tending to cause hypertension of the knee joint; and a fifth pressure sensor located on the second terminal member proximate the second rigid support member and providing a fifth pressure signal in response to the force tending to cause hypertension of the knee joint.

15. The brace of claim 14, wherein the sensor means further includes programmable processor means operably connected to each of the first, second, third, fourth and fifth pressure sensors and to the inflation means for programming a threshold sensitivity for each of the first, second, third, fourth and fifth pressure sensors and for providing the trigger signal in response to a programmed set of the first, second, third, fourth and fifth pressure signals.

16. The brace of claim 9, wherein the support means further includes a semi-rigid, first anterior cuff having an edge secured to the first rigid support member and an opposing vertex pivotally connected to the second terminal member, and a semi-rigid, second anterior cuff having an edge secured to the second rigid support member and an opposing vertex pivotally connected to the first terminal member, and wherein the sensor means includes at least one of the following:

a first strain sensor, attached to the first anterior cuff and having a first connection to the first rigid support member at a location spaced apart from the first terminal member and a second connection to the second terminal member, providing a first strain signal in response to a strain condition between the first rigid support member and the second terminal member; and a second strain sensor, attached to the second anterior cuff and having a first connection to the second rigid support member at a location spaced apart from the second terminal member and a second connection to the first terminal member, providing a second strain signal in response to a strain condition between the second rigid support member and the second terminal member.

17. The brace of claim 16, wherein the sensor means further includes at least one of the following:

a first pressure sensor located on a medial side of the posterior strut and adapted to face the knee joint and providing a first pressure signal in response to a medial force on the knee joint;

a second pressure sensor located on a lateral side of the posterior strut and adapted to face the knee joint and providing a second pressure signal in response to a lateral force on the knee joint;

a third pressure sensor located on the posterior strut and adapted to be positioned in the popliteal space facing the joint and providing a third pressure signal in response to a posterior force on the knee joint;

a fourth pressure sensor located on the first terminal member proximate the first rigid support member and providing a fourth pressure signal in response to a force tending to cause hypertension of the knee joint; and a fifth pressure sensor located on the second terminal member proximate the second rigid support member and providing a fifth pressure signal in response to the force tending to cause hyperextension of the knee joint.

18. The brace of claim 17, wherein the sensor means further includes programmable processor means operably connected to each of the first, second, third, fourth and fifth pressure sensors, to the first and second strain sensors and to the inflation means for programming a threshold sensitivity for each of the first, second, third, fourth and fifth pressure sensors and each of the first and second strain sensors and for providing the trigger signal in response to a programmed set of the first, second, third, fourth and fifth pressure signals and the first and second strain signals.

19. The brace of claim 18, wherein the inflation means includes a canister containing a material for inflating the inflatable air bag, and valve means for providing operative connection between the inflation means and the canister in response to the trigger signal.

20. The brace of claim 19, wherein the valve means includes deflation means for deflating the inflatable air bag.

21. The brace of claim 17, further comprising muscle stimulator means adapted to be located adjacent a muscle connected to the knee joint for stimulating the muscle in response to at least one of the first, second, third, fourth and fifth pressure signals and the first and second strain signals.

22. An orthopaedic brace for a joint, comprising:

support means for providing support to the joint and for permitting a predetermined range of movement of the joint, said support means being spaced apart from said joint and defining a void space about encircling the joint;

sensor means attached to the support means for providing a trigger signal in response to a predetermined condition on the joint that is capable of injuring the joint, said predetermined condition being selected from a group consisting of, pressure, strain, stress and acceleration;

muscle stimulator means adapted to be located adjacent a muscle connected to the joint for stimulating the muscle in response to the trigger signal such that the muscle is preloaded for protecting the joint from injury;

an inflatable air bag in the void space; and inflation means operably connected to the sensor means and the air bag for inflating the air bag in response to the trigger signal.

* * * * *

UNITED STATES PATENT AND TRADEMARK OFFICE
CERTIFICATE OF CORRECTION

PATENT NO. : 5,558,627
DATED : September 24, 1996
INVENTOR(S) : SAMUEL SINGER et al.

It is certified that error appears in the above-indentified patent and that said Letters Patent is hereby corrected as shown below:

```
Column 6, line 23, "LOS" should be --108--;
          line 38, "joint L" should be --joint 1--;
          line 40, "joint L" should be --joint 1--; and
          line 42, "joint L" should be --joint 1--.
```

In Claim 14, Column 9, lines 53 and 57, "hypertension" should be --hyperextension--.

In Claim 17, Column 10, line 40, "hypertension" should be --hyperextension--.

Signed and Sealed this

Twenty-seventh Day of May, 1997

Attest:

BRUCE LEHMAN

*Attesting Officer*     *Commissioner of Patents and Trademarks*